(12) United States Patent
Randall

(10) Patent No.: US 11,249,048 B2
(45) Date of Patent: Feb. 15, 2022

(54) DETECTING PARTICLES IN A PARTICLE CONTAINING FLUID

(71) Applicant: Parker Hannifin EMEA S.à.r.l., Etoy (CH)

(72) Inventor: Neil Randall, West Sussex (GB)

(73) Assignee: Parker Hannifin EMEA S.à.r.l., Etoy (CH)

( * ) Notice: Subject to any disclaimer, the term of this patent is extended or adjusted under 35 U.S.C. 154(b) by 32 days.

(21) Appl. No.: 16/876,213

(22) Filed: May 18, 2020

(65) Prior Publication Data

US 2020/0278322 A1    Sep. 3, 2020

Related U.S. Application Data

(63) Continuation of application No. PCT/EP2018/082689, filed on Nov. 27, 2018.

(30) Foreign Application Priority Data

Dec. 5, 2017   (GB) ..................... 1720276

(51) Int. Cl.
*G01N 29/22* (2006.01)
*G01N 29/02* (2006.01)
(Continued)

(52) U.S. Cl.
CPC ............. *G01N 29/02* (2013.01); *G01N 15/02* (2013.01); *G01N 15/06* (2013.01); *G01N 29/22* (2013.01);
(Continued)

(58) Field of Classification Search
CPC ........ G01N 29/02; G01N 29/22; G01N 29/36; G01N 29/4427; G01N 29/265;
(Continued)

(56) References Cited

U.S. PATENT DOCUMENTS 3,844,174 A    10/1974   Chabre
4,269,696 A *  5/1981   Metrailer ............... C10G 11/18
                                                        201/38
(Continued)

FOREIGN PATENT DOCUMENTS

EP         2 246 698 B1    6/2012
GB         2 431 993 A     5/2007
JP         2007113916 A    5/2007

OTHER PUBLICATIONS

International Search Report and Written Opinion for PCT/EP2018/082689 dated Mar. 27, 2019.
(Continued)

*Primary Examiner* — Suman K Nath
(74) *Attorney, Agent, or Firm* — Christopher H. Hunter

(57) ABSTRACT

A sensor system for detecting particles within a fluid, the sensor system comprising: i) a gauge body having a working surface for receiving a particle containing fluid; ii) an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and iii) a sensor configured to detect the signal generated by the particles impacting the impactor and provide an output signal.

21 Claims, 8 Drawing Sheets

(51) Int. Cl.
　　　*G01N 15/02*　　　(2006.01)
　　　*G01N 15/06*　　　(2006.01)
　　　*G01N 29/36*　　　(2006.01)
　　　*G01N 33/28*　　　(2006.01)
(52) U.S. Cl.
　　　CPC ............. *G01N 29/36* (2013.01); *G01N 33/28* (2013.01); *G01N 2291/0226* (2013.01); *G01N 2291/02827* (2013.01)
(58) Field of Classification Search
　　　CPC ...... G01N 29/27; G01N 29/14; G01N 29/046; G01N 2291/0226; G01N 2291/02827; G01N 2291/02416; G01N 2291/02809; G01N 33/28; G01N 33/2835; G01N 33/2858; G01N 15/02; G01N 15/06; G01N 2015/0053; G01N 2015/0261
　　　See application file for complete search history.

(56) References Cited

U.S. PATENT DOCUMENTS

| | | | |
|---|---|---|---|
| 4,315,428 | A | 2/1982 | Stuivenwold |
| 4,674,337 | A | 6/1987 | Jonas |
| 7,286,633 | B1 | 10/2007 | Hardman |
| 2002/0067485 | A1 | 6/2002 | Hatfield |
| 2007/0241637 | A1* | 10/2007 | Kalantar-Zadeh ... G01N 29/022 310/313 D |
| 2015/0075301 | A1* | 3/2015 | Scialo .................. G01N 1/2208 73/863.22 |
| 2015/0191660 | A1 | 7/2015 | Englund |
| 2017/0192117 | A1 | 7/2017 | D'Angelo |

OTHER PUBLICATIONS

Combined Search and Examination Report for GB 17020276.3 dated May 29, 2018.
MK Sorenson et al.; "NMR sensor for onboard ship detection of catalytic fines in marine fuel oils", Abstract, Anal Chem. Aug. 5, 2014;86(15):7205-8. doi: 10.1021/ac5014496. Epub Jul. 17, 2014.
Bejer, Artur et al.; "Analysis of tribological processes occuring in precision pairs based on example of fuel injection pumps of marine diesel engines", Scientific Journals of the Maritime University of Szczecin, 2015, 41 (113), 9-16.
Bsangya, Allan et al,; "An acoustic method for the measurement of minimum fluidization and bubbling properties of group a solids", Particulate Solid Research, Inc., Chicago, IL 60632, Conference Paper Jan. 2014.
Communication Pursuant to Rules 161(1) and 162 EPC for EP 18808354.7 dated Jul. 14, 2020.
Response to Communication Pursuant to Rules 161(1) and 162 EPC for EP 18808354.7 dated Jan. 5, 2021.

* cited by examiner

DETECTING PARTICLES IN A PARTICLE CONTAINING FLUID

FIELD OF INVENTION

The present specification relates to sensor systems and methods for detecting particles in particle containing fluids. Particular applications include detecting catalytic particles (also known as catalytic fines or cat fines) in marine fuel oil.

BACKGROUND OF INVENTION

Zeolite catalysts can be used in the refining of crude oil. The majority of this material can be reclaimed and re-used in the refinery. The low-grade residual output from the refining process is routinely sold as marine fuel which contains some catalytic fines. As such, much of the heavy fuel oil burnt in the cylinders of large 2-stroke marine diesel engines is contaminated with hard particles (catalytic fines). Catalytic fines can include hard aluminium and silicon oxide particles that are normally present in such heavy fuel oil. The fines can comprise particles of spent aluminium and silicon catalyst that arise from the catalytic cracking process in the refinery. For refineries relying on catalytic cracking, catalytic fines are added to the crude oil to enhance low temperature fuel cracking. The fines can include complex alumino-silicates and, depending on the catalyst used, vary both in size and hardness. If not reduced by suitable treatment, the abrasive nature of these fines will damage the engine, particularly fuel pumps, injectors, piston rings and liners.

Hard particles, which find their way into the fuel at the oil refinery, can cause catastrophic abrasive damage to engine cylinder liners during the combustion process. This problem has been inadvertently exacerbated by changes to the regulation of marine air pollution because it has driven the use of cat-fine prone, low-sulphur fuel oils. As a means of self-preservation, vessels collect representative fuel samples during bunkering and then send them off for laboratory analysis. However, the test results often only become available once a ship has set sail and is far out to sea, by which time significant engine damage may already be in progress.

Catalytic fines tests have been developed to flag up heavy fuel oil samples that may be contaminated with dangerous levels of catalytic fines before the fuel has been pumped aboard a vessel. Tests are capable of identifying those fuel samples that have a catalytic fine concentration of >60 ppm (Al+Si) and which therefore exceed the limit recommended by ISO 8217:2012. This level, and indeed much lower levels, can be measured using Inductively Coupled Plasma Atomic Emission Spectroscopy. However, this is a complex analysis carried out at a land-based laboratory. Such tests have been specifically designed to provide the crew of a vessel with a clear sail or don't sail indication with regard to fuel quality.

Once the fuel is on board, the catalytic fines content has to be reduced to a level around 10 to 15 ppm before it enters the engine as the catalytic fines are very abrasive and cause serious damage, even at very low concentrations. This is achieved using a combination of settling tanks, purifiers and filters. There is a need for a method, suitable for use on board, that can be used for checking the operation of this system. There are several products available including: Parker's Cat Fines Kit; NanoNord's Cat Guard; CMT's Cat Fines Tester; and Martechnic's Cat Fines Check. Information regarding these systems is available via the internet.

Several currently available techniques for detecting particles in particle containing fluids are briefly discussed below.

U.S. Pat. No. 9,759,706 discloses a kit and method for monitoring the presence of catalyst fines in heavy fuel oil (HFO), including: (a) providing a sample of HFO; (b) mixing the HFO sample with a diluent composition comprising a non-polar solvent and with an aqueous reagent composition to provide a test sample, wherein the aqueous reagent composition comprises at least one water soluble inorganic salt and at least one water soluble base; (c) allowing phase separation to occur in the test sample to provide an aqueous phase and an organic phase; and (d) inspecting the aqueous phase of the test sample for the presence of catalyst fines.

U.S. Pat. No. 9,714,909 discloses a method of performing a quantitative and/or qualitative determination of catalytic fines in fuel oil and a system suitable for determining catalytic fines in an oil using the method. The method comprises determining aluminum using NMR and quantitatively and/or qualitatively determining the catalytic fines based on the aluminum determination. The system comprises an NMR spectrometer, a digital memory storing a calibration map comprising calibrating data for calibrating NMR spectra obtained by the NMR spectrometer and a computer programmed to analyze the NMR spectra obtained by the NMR spectrometer using the calibration map and performing at least one quantitative and/or qualitative catalytic fines determination.

EP 3121596 discloses a method for determining the content of catalyst fines in a sample of a heavy oil, in particular a fuel for marine engines, including the following steps: (a) a sample is taken from the heavy oil; (b) the sample is placed in a first vessel with a first reagent and intensively mixed; (c) a portion of the mixture of the first container is introduced into a second container comprising dilute hydrochloric acid reagent and mixed intensively with the hydrochloric acid; (d) from the second container, a portion of the content is removed; and (e) in a third container, the content of catalyst fines in the sample is determined by determining the strength of the resulting fluorescence radiation in UV light excitation, the fluorescence radiation being detected visually or by means of a photometer.

EP 2246698 discloses the use of ultrasonics to detect catalytic fines. The technique involves launching an ultrasonic pulse into a sample and detecting this pulse after it has travelled through the sample. The presence of catalytic fine particles effects the characteristics of the detected pulse.

US 2015/0191660 discloses a method for separating catalytic fines from an oil stream comprising the steps of: separating catalyst fines from an inlet oil stream in a centrifugal separator to generate a stream of purified oil; obtaining a nuclear magnetic resonance (NMR) response signal from an NMR apparatus related to the amount of catalyst fines in the purified oil stream and/or the inlet oil stream; and initiating the addition of, or increasing the amount of, a separation aid to the inlet oil stream when the NMR response signal indicates an increased amount of catalyst fines in the purified oil stream and/or the inlet oil stream, to increase the performance of separating catalyst fines from the oil stream.

U.S. Pat. No. 7,286,633 discloses a fuel analysis system and method wherein an x-ray source emits x-rays at an energy level below but proximate the absorption edge of sulfur. A monochromator is provided in the optical path between the source and a fuel sample for directing x-rays at a single energy level at the fuel sample to limit excitation of any sulfur in the fuel sample. A detector is responsive to x-rays emitted by the sample and an analyzer is responsive to the detector and configured to determine the amount of silicon and aluminum in the sample.

Bejger et al. (Scientific Journals of the Maritime University of Szczecin, 2015, 41 (113), 9-16) provide an analysis of tribological processes occurring in fuel injection pumps of marine diesel engines. It is indicated that issues concerning fuel injection pump diagnosis using acoustic emission signals are under study. Further publications indicate the use of acoustic emission signals to detect worn injectors including the use of acoustic emission to monitor the turbulent flow of fuel in the injector with the acoustic emission signature from the injector changing as it wears. Other documents also disclose the use of acoustic emission signals to detect lubrication problems in bearings and other lubricated mechanical components such as gears.

Despite the above, there is still a need to provide a sensor system and methodology which meets a number of criteria for detecting catalytic fines in marine fuel oil including:
high sensitivity to low levels of particulate contamination;
relatively inexpensive equipment;
simple to use; and
suitable for use on board ships.

There are no known currently available products that adequately meet all of these criteria. As such, it is an aim of the present invention to provide a sensor system and method which meets all of these criteria. It is also an aim of the present invention to provide a sensor system and method which is suitable for other applications which require the same or a similar set of performance characteristics for detecting particles within a fluid including applications which utilize Newtonian fluids (gases and liquids) and non-Newtonian fluids such as greases and the like.

SUMMARY OF INVENTION

A sensor system for detecting particles within a fluid is provided, the sensor system comprising:
i. a gauge body having a working surface for receiving a particle containing fluid;
ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
iii. a sensor configured to detect the signal generated by the particles impacting the impactor and provide an output signal.

It has been found that in such a sensor system configuration, the sensor can be configured to detect elastic waves generated by particles impacting the impactor. The sensor may be in the form of an acoustic emission sensor, an accelerometer, an ultrasonic sensor, or a corresponding sensor device suitable for detecting the particle impacts and generating an output signal indicative of one or both of the size and concentration of particles in the fluid. Such a sensor can be mounted on, or embedded within, the gauge body or the impactor. Particle impacts can be generated in a number of ways. For example, the impactor can be moved across the working surface of the gauge body, whereby particles disposed over the working surface are impacted by the impactor to generate the signal as fluid passes through the spacing between the impactor and the working surface of the gauge body. Alternatively, or additionally, the sensor system can be configured such that the particle containing fluid is forcibly flowed through the spacing between the impactor and the working surface of the gauge body to cause particles to be impacted by the impactor. Examples of such configurations are given in the detailed description.

A method of sensing particles in a particle containing fluid is also provided, the method comprising:
i. loading a particle containing fluid onto a working surface of a gauge body;
ii. providing an impactor spaced apart from the working surface of the gauge body defining a spacing between the impactor and the working surface of the gauge body through which particle containing fluid can pass, wherein as the particle containing fluid passes through the spacing between the impactor and the working surface of the gauge body, particles disposed over the working surface are impacted by the impactor generating a signal which is dependent on one or both of the size and concentration of particles in the fluid; and
iii. detecting the signal generated by the particles impacting the impactor and providing an output signal.

The methodology as described herein is a passive technique in that a sensor is used to detect elastic waves (e.g. high frequency structural sounds) produced by mechanical impacts. It has been found that such a configuration can be used to detect impacts produced when oil contaminated with catalytic fines is caused to flow between two surfaces, e.g. two metal surfaces. The technique has been found to be very sensitive to low levels of contamination and can be used to confirm the correct operation of separators used to clean fuel oil. In particular, the technique has been found to meet all the criteria as outlined in the background section: (i) high sensitivity to low levels of particulate contamination; (ii) relatively inexpensive equipment; (iii) simple to use; and (iv) suitable for use on board ships. Furthermore, it is envisaged that the sensor system and method as described herein will be suitable for other applications which require the same or a similar set of performance characteristics for detecting particles within a fluid.

BRIEF DESCRIPTION OF THE DRAWINGS

Embodiments of the present invention are described by way of example only with reference to the accompanying drawings in which.

DETAILED DESCRIPTION

Figure 1:
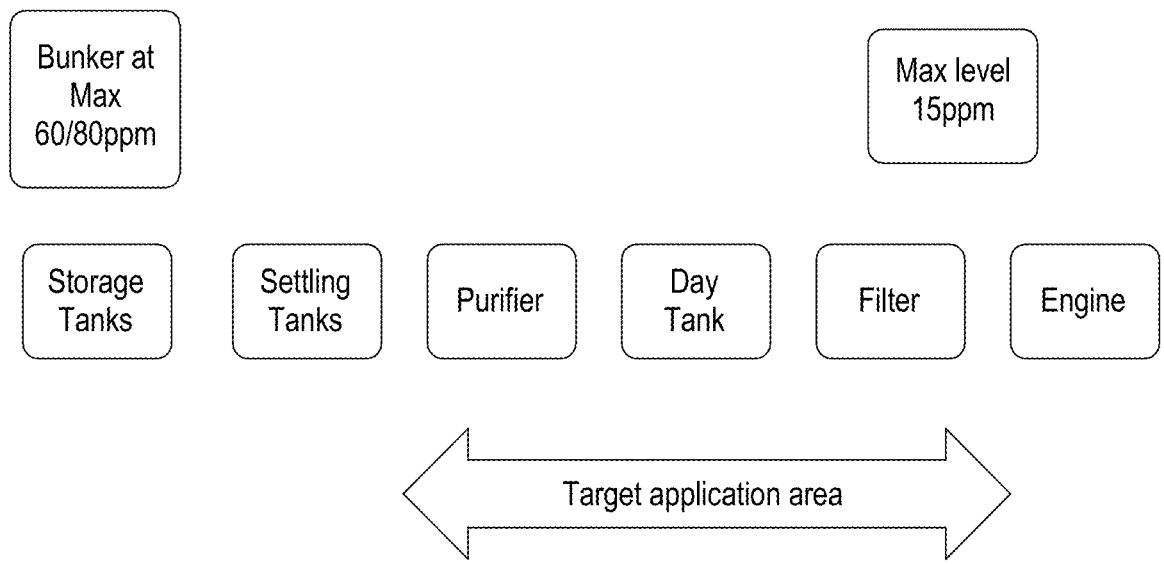
FIG. 1 shows a flow diagram of a process for managing catalytic fines in marine fuel oil.
Figure 2A:
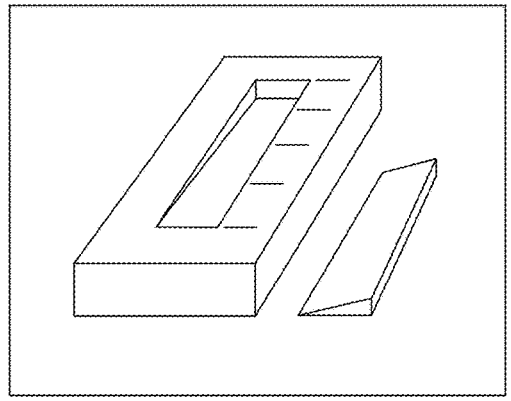
FIG. 2(a) illustrates a standard Hegman gauge.
Figure 2B:
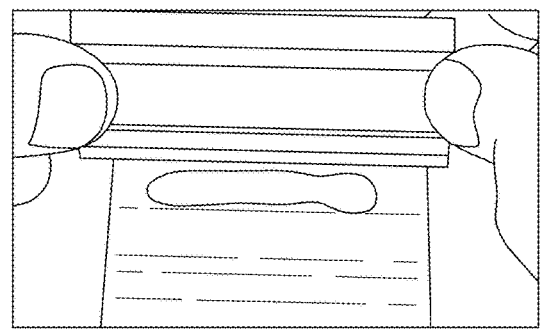
FIG. 2(b) illustrates a first step in the use of the Hegman gauge of FIG. 2(a)
Figure 2C:
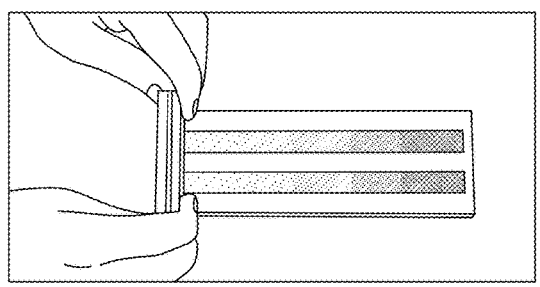
FIG. 2(c) illustrates a further step in the use of the Hegman gauge of FIG. 2(a)
Figure 2D:
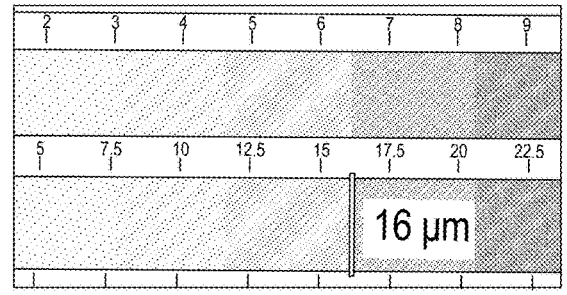
FIG. 2(d) illustrates a scale along the Hegman gauge of FIG. 2(a)

FIG. 1 shows a flow diagram of a process for managing catalytic fines in marine fuel oil on board a ship. Fuel oil is supplied to ships (known as bunkering) with a maximum catalytic fine concentration of the order of 60 to 80 ppm. The fuel oil is stored in one or more storage tanks on a vessel and requires further processing prior to use. In particular, once the fuel is on board the catalytic fines content has to be reduced to a level around 10 to 15 ppm before it enters the engine. This is achieved using a combination of settling tanks, purifiers, and filters. For example, as shown in FIG. 1, fuel oil from the storage tanks can be introduced into settling tanks and then processed through a purifier prior to storage in a day tank. The purified fuel oil can then be filtered prior to introduction into the engine. After filtering, the maximum level of catalytic fines should be around 10 to 15 ppm. Purifiers and filters can be selected in order to achieve the target level. However, purifiers and filters degrade in performance over time and thus it is required to be able to detect these low levels of catalytic fines during operation of the process and provide maintenance to the system if levels increase so as to avoid damaging the engine of the vessel.

As described in the summary of invention section, a sensor system for detecting particles within a fluid is provided, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal.

It has been found that in such a sensor system configuration, the sensor can be configured to detect elastic waves generated by particles impacting the impactor. The sensor may be in the form of an acoustic emission sensor, an accelerometer, an ultrasonic sensor, or a corresponding sensor device suitable for detecting the particle impacts and generating an output signal indicative of one or both of the size and concentration of particles in the fluid. Such a sensor can be mounted on, or embedded within, the gauge body or the impactor.

Particle impacts can be generated in a number of ways. For example, in one configuration the impactor can be moved across the working surface of the gauge body, whereby particles disposed over the working surface are impacted by the impactor to generate the signal as fluid passes through the spacing between the impactor and the working surface of the gauge body. The signal is generated by particles which have a size exceeding the spacing between the impactor and the working surface of the gauge body as the impactor is moved across the working surface. Particles in the fluid become trapped between the impactor and the working surface and such impacts generate the signal.

The size of the spacing can be set at a suitable distance to detect particles of a target size or size range. If a fixed spacing is provided, then particles larger than the spacing can be detected although in such a configuration details of particle size distribution are minimal. In an improved configuration, the impactor is configured to be movable across the working surface of the gauge body in such a manner that the spacing between the impactor and the working surface decreases on moving the impactor across the working surface. For example, the working surface of the gauge body can be sloped (e.g. a continuous smooth slope) or stepped such that the spacing between the impactor and the working surface decreases on moving the impactor across the working surface. In such a configuration, the spacing between the impactor and the working surface will be dependent on the location of the impactor over the working surface. The size of the particles impacting the impactor will thus be dependent on the location of the impactor over the working surface. The signal from different sized particles can thus be time resolved giving more information about the size distribution of particles in the fluid. That is, one can obtain information about both the size and concentration of particles in the fluid.

In another configuration, the impactor can be supported over the working surface of the gauge body by a guide rail which is sloped relative to the working surface such that the spacing between the impactor and the base decreases on moving the impactor across the working surface. This alternative configuration will have the same advantage that the size of the particles impacting the impactor will be dependent on the location of the impactor across the working surface.

In one configuration, the gauge body comprises a channel, the channel having a first end, a second end, and a base forming the working surface for receiving the particle containing fluid, the impactor being configured to be movable along the channel in a direction from the first end to the second end whereby particles within the channel are impacted by the impactor generating the signal. In this case, the base of the channel may be sloped or stepped, or a sloped guide rail may be provided as previously described in order to provide a variable spacing. The impactor is configured to be movable along the channel in a direction from the first end to the second end with the spacing between the impactor and the base of the channel decreasing on moving the impactor from the first end to the second end of the channel. Particles within the channel are impacted by the impactor generating the signal which is dependent on the size and concentration of particles in the fluid.

The gauge body may have more than one such channel. A gauge body may be provided with a plurality of channels having different depths to interrogate particles of different sizes. For example, the gauge body may have one or more channels having a depth between 0 and 100 micrometres, 0 and 50 micrometres, 0 and 25 micrometres, 0 and 15 micrometres, or 0 and 10 micrometres.

The impactor can be in the form of a slider which slides over the working surface of the gauge body (e.g. under gravity or driven via a suitable drive mechanism. Alternatively, the impactor can be in the form of a roller which rolls over the working surface of the gauge body.

Alternatively, or additionally, the sensor system can be configured such that the particle containing fluid is forcibly flowed through the spacing between the impactor and the working surface of the gauge body to cause particles to be impacted by the impactor. In such a configuration, the spacing can be in the form of an aperture which can be varied in size in order to detect particles of differing size.

The gauge body can be provided by a Hegman gauge or variant thereof. A Hegman gauge is show in FIGS. 2(a) to 2(d) in its standard usage for determine how finely ground the particles of pigment are dispersed in a sample of paint. The gauge consists of a steel block with a series of very small parallel grooves machined into it. The grooves decrease in depth from one end of the block to the other, according to a scale stamped next to them. Hegman gauges are commonly available in the following ranges: 0 to 100 micrometres, 0 to 50 micrometres, 0 to 25 micrometres, 0 to 15 micrometres, and 0 to 10 micrometres.

In its conventional application, a Hegman gauge is used by puddling a sample of paint at the deep end of the gauge and drawing the paint down with a flat edge along the grooves. The paint fills the grooves, and the location where a regular, significant "pepperyness" in the appearance of the coating appears, marks the coarsest-ground dispersed particles. The reading is taken from the scale marked next to the grooves, in dimensionless "Hegman units" and/or mils or micrometres. Determining the fineness of a paint's grind is important, because too coarse a grind may reduce the paint's color uniformity, gloss, and opacity. The Hegman gauge is widely used for this purpose because it requires minimal skill and only a few seconds' work.

Figure 3A:
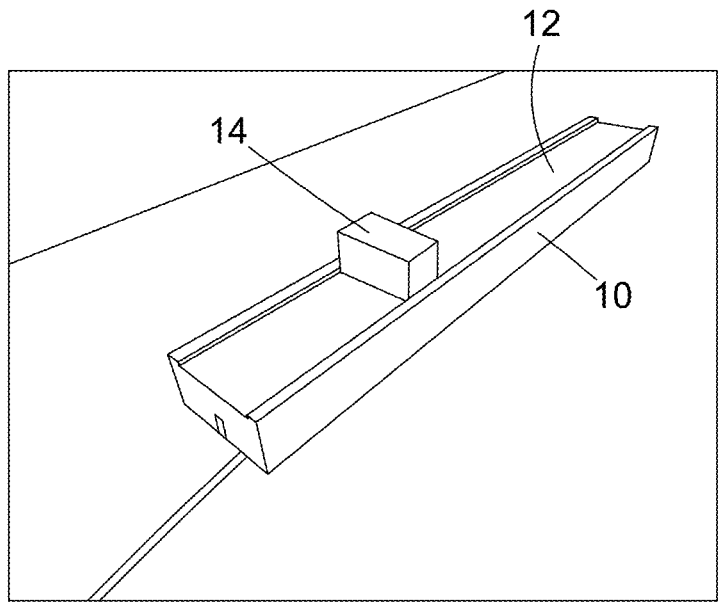
FIG. 3(a) shows a rear view of the sensor system for detecting particles in a fluid comprising a Hegman gauge type gauge body and an acoustic emission sensor mounted in the gauge body.
Figure 3B:
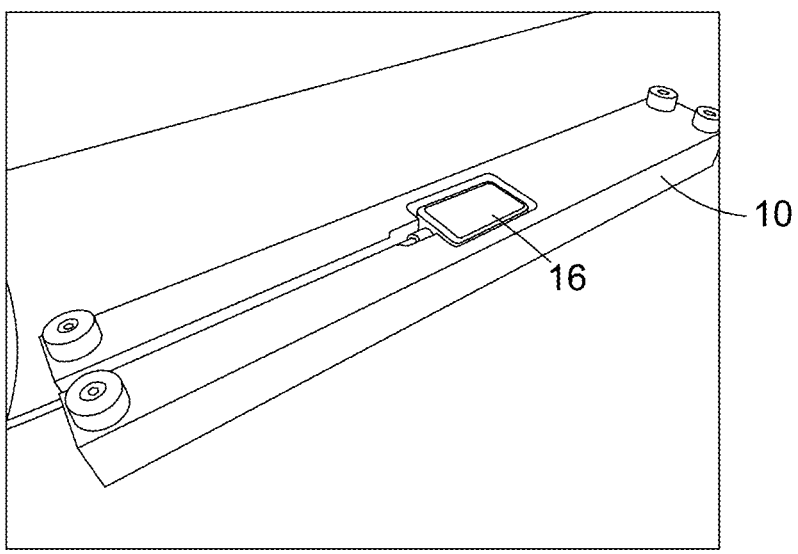
FIG. 3(b) shows a rear view of the sensor system of FIG. 3(a)

The present inventors have surprisingly found that incorporating an acoustic emission sensor into a Hegman gauge transforms its capabilities to enable detection of catalytic fines in fuel oil at levels below 10 ppm. FIGS. 3(a) and 3(b) show front and rear views of such a modified sensor system. The sensor system comprises a gauge body 10 in the form of a metal block having a surface 12 in which an elongate channel is formed. The channel has a decreasing depth along its length. Optionally, a set of indicia are provided along the channel corresponding to the depth of the channel along its length.

A slider 14 having an edge with a length larger than the width of the channel is movable along the surface 12, whereby when liquid is located within the channel and the slider 14 is moved along the channel in the direction of decreasing depth, an edge of the slider contacts the fluid across the channel and forces the fluid into the channel and between the channel base and the underside of the slider. Particles within the channel impact the leading edge of the slider when a particle dimension exceeds the depth of the channel under the slider. As shown in FIG. 3(b), an acoustic sensor 16 is embedded within the gauge body 10 to acoustically sense particles impacting the slider and provide an output signal. The signal can be correlated to the indicia on the plate to calculate the size of particles within the fluid. The magnitude and/or number of the signals for a specific size or size band can be correlated to the concentration of particles within the fluid. The acoustic sensor can readily be calibrated using a set of standardized particles containing fluids to give an output signal indicating particle concentrations, particle sizes, and/or particle size distributions.

In accordance with one methodology, oil is diluted with a solvent to reduce its viscosity. This solution is then spread onto the active surface of the gauge body. The surface of the gauge body has a trough machined into it, the depth of the trough decreasing along its length. A metal block slides down the length of the gauge body, e.g. under gravity. As it does so the gap between the block and the bottom of the trough decreases. If the oil contains hard particles such as catalytic fines, they will start to impact on the metal block when their diameter exceeds the available depth in the trough. These impacts produce bursts of high frequency sound which travel through the structure of the gauge body and are picked up by an acoustic emission sensor. The total pulse count provides a measure of the abrasiveness of the fuel. An audio output lets an operator listen to the impacts as they occur if desired. Alternatively, or additionally, the acoustic sensor can be calibrated to give a graphical or numerical readout.

In the configuration described above, a channel of decreasing depth is provided to form the working surface of the gauge body. However, other configurations are possible. For example, the channel depth may be constant, and the impactor supported over the working surface of the gauge body by a guide rail which is sloped relative to the working surface such that the spacing between the impactor and the base decreases on moving the impactor across the working surface. Alternatively, still, as previously indicated, the spacing may remain constant although such configurations give less information about the size distribution of the particles in the fluid.

A channel is not necessarily required so long as the working surface of the gauge body and the impactor are configured such that movement of one component relative to the other results in a decrease in the spacing to cause impacting of particles of varying size generating acoustic signals. In this case, the spacing between impactor and working surface may fall between any one or more of the preceding ranges. Furthermore, movement of the impactor may be under gravity or via any suitable drive mechanism. Further still, the impactor may be secured to the gauge body or may merely sit on the gauge body with the weight of the impactor holding the configuration together in use.

Other variants are also envisaged. For example, the sensor could be mounted on, or embedded within, the impactor rather than the gauge body. Furthermore, the acoustic emission sensor can be calibrated to provide an output signal which indicates particle size and/or particle concentration without the provision of indicia on the gauge body. While the impactor can be in the form of a metal block which slides over the working surface of the gauge body, the impactor could be provided in the form of a roller or other configuration.

Furthermore, while the aforementioned configurations involve moving the impactor over the working surface of the gauge, is it also envisaged that the impacts can be generated using an on-line flow configuration in which the sensor system is configured such that the particle containing fluid is forcibly flowed through the spacing between the impactor and the working surface of the gauge body to cause particles to be impacted by the impactor thereby generating the signal. In such a flow cell type configuration, the spacing can be in the form of an aperture which can be varied in size in order to detect particles of differing size via variations in the impact signal.

The gauge body and impactor should ideally be formed of a material have a high Vickers hardness. Hard materials will improve wear resistance and also aid in generating and transmitting a strong acoustic signal to the acoustic emission sensor. Suitable materials include metals, alloys, ceramics, carbides, diamond (and other super-hard materials), and/or components which are coated with a wear resistant coating of such materials.

As previously described, the basic methodology comprises:
i. loading a particle containing fluid onto a working surface of a gauge body;
ii. providing an impactor spaced apart from the working surface of the gauge body defining a spacing between the impactor and the working surface of the gauge body through which particle containing fluid can pass, wherein as the particle containing fluid passes through the spacing between the impactor and the working surface of the gauge body, particles disposed over the working surface are impacted by the impactor generating a signal which is dependent on one or both of the size and concentration of particles in the fluid; and
iii. detecting the signal generated by the particles impacting the impactor and providing an output signal.

For example, the method may comprise moving an impactor across the working surface of the gauge body such that a spacing between the impactor and the working surface decreases on moving the impactor across the working surface whereby particles disposed over the working surface are impacted by the impactor generating an acoustic signal which is dependent on the size and concentration of particles in the fluid.

The methodology as described herein is a passive technique in the sense that an acoustic emission sensor is used to detect high frequency structural sounds produced by mechanical impacts. Prior art references show various techniques using X-rays, ultrasonics, or acoustic wave patterns for identifying particles within a fluid stream, including catalytic fines. However, none appear to suggest the use of a gauge body (such as a Hegman type gauge) and an acoustic sensor mounted in or on the gauge body to sense when particles impact a slider when the slider is forced along the surface of the gauge body and across a channel of decreasing depth with a particle containing fluid located within the channel.

Figure 4:
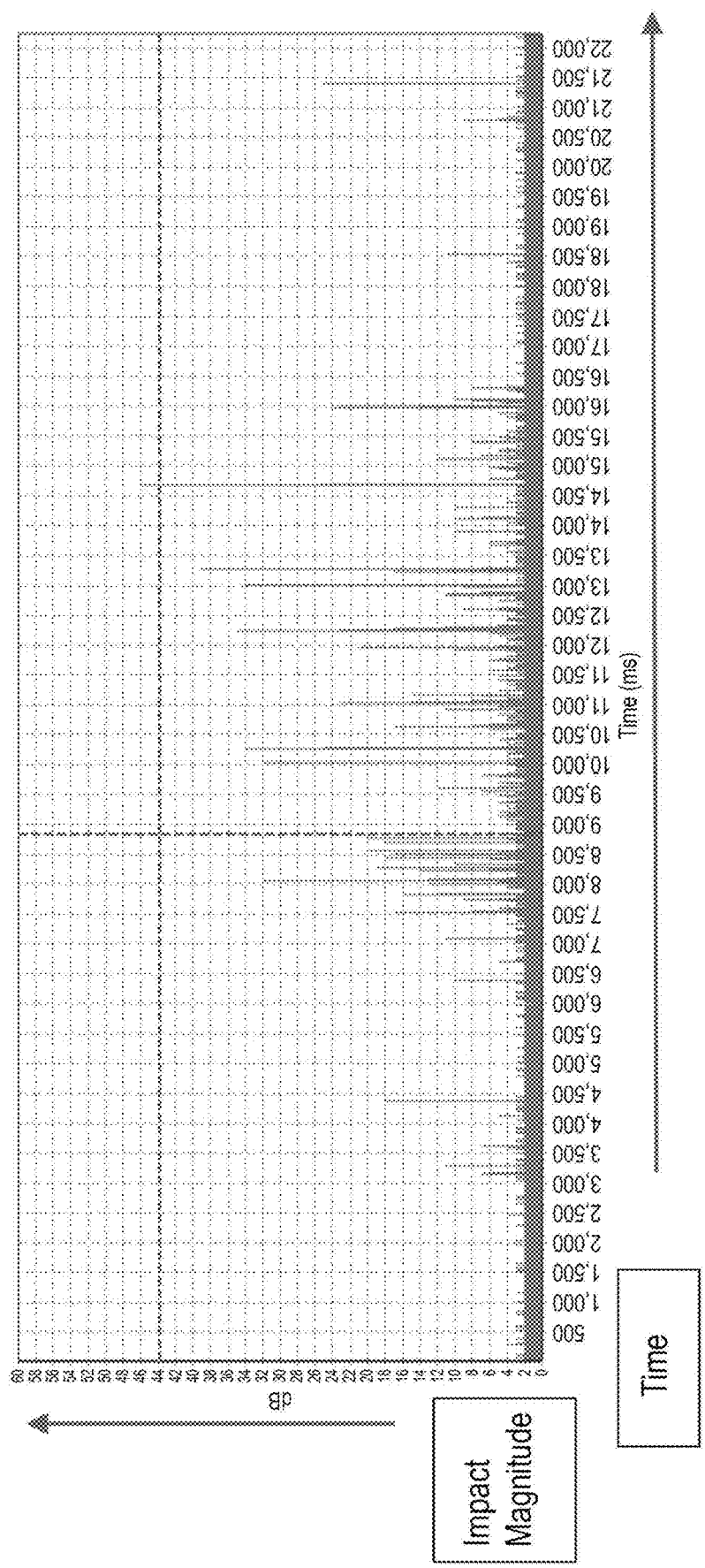
FIG. 4 shows the sensor system output for a fuel oil sample pre-purifier in the process flow of FIG. 1.
Figure 5:
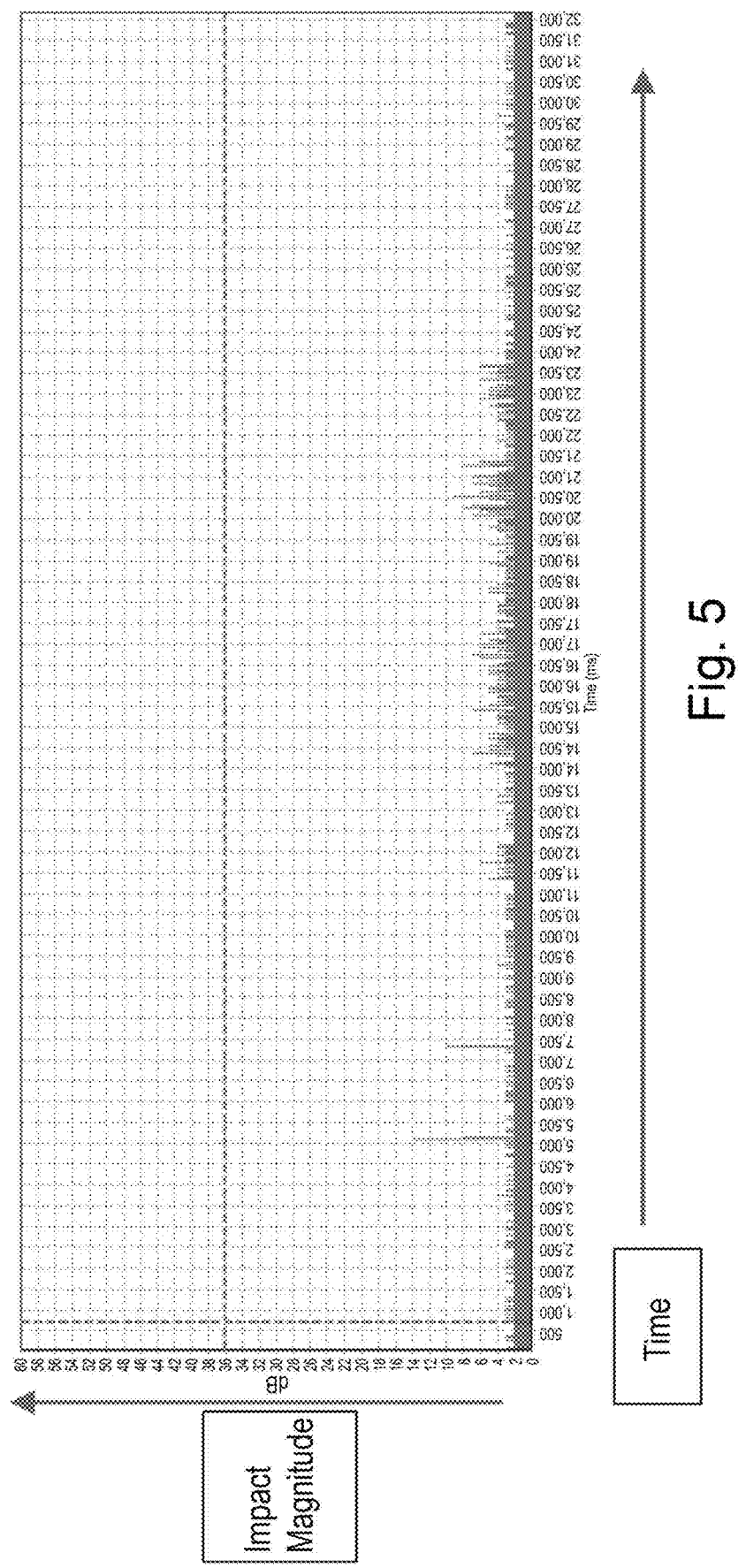
FIG. 5 shows the sensor system output for a fuel oil sample post-purifier in the process flow of FIG. 1.
Figure 6:
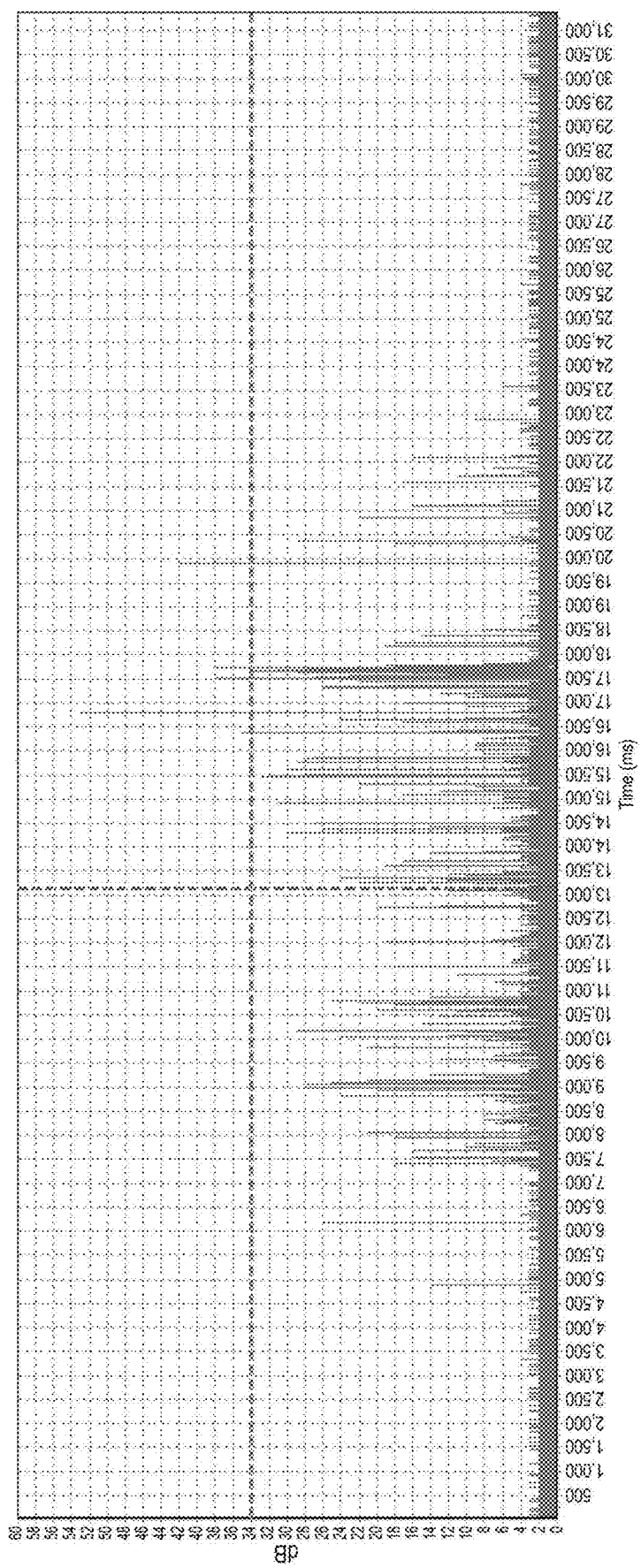
FIG. 6 shows the sensor system output for a fuel oil bunker sample in the process flow of FIG. 1 with an additional 30 ppm of dry fines added.

FIG. 4 shows the sensor system output for a fuel oil sample pre-purifier in the process flow of FIG. 1. The graph illustrates acoustic data plotted as intensity (in decibels, dB) versus time (in milliseconds, ms) which can be equated to the position of the impactor along the gauge body and thus to the size of particles causing the impact signals. FIG. 5 shows the sensor system output for a fuel oil sample post-purifier in the process flow of FIG. 1. As is clear, the number and intensity of impact signals is much reduced indicating the reduction in catalytic fine content after purification. Conversely, FIG. 6 shows the sensor system output for a fuel oil bunker sample in the process flow of FIG. 1 with an additional 30 ppm of dry fines added. As is clear, the number and intensity of impact signals is much increased indicative of the increase in catalytic fine content.

Figure 7:
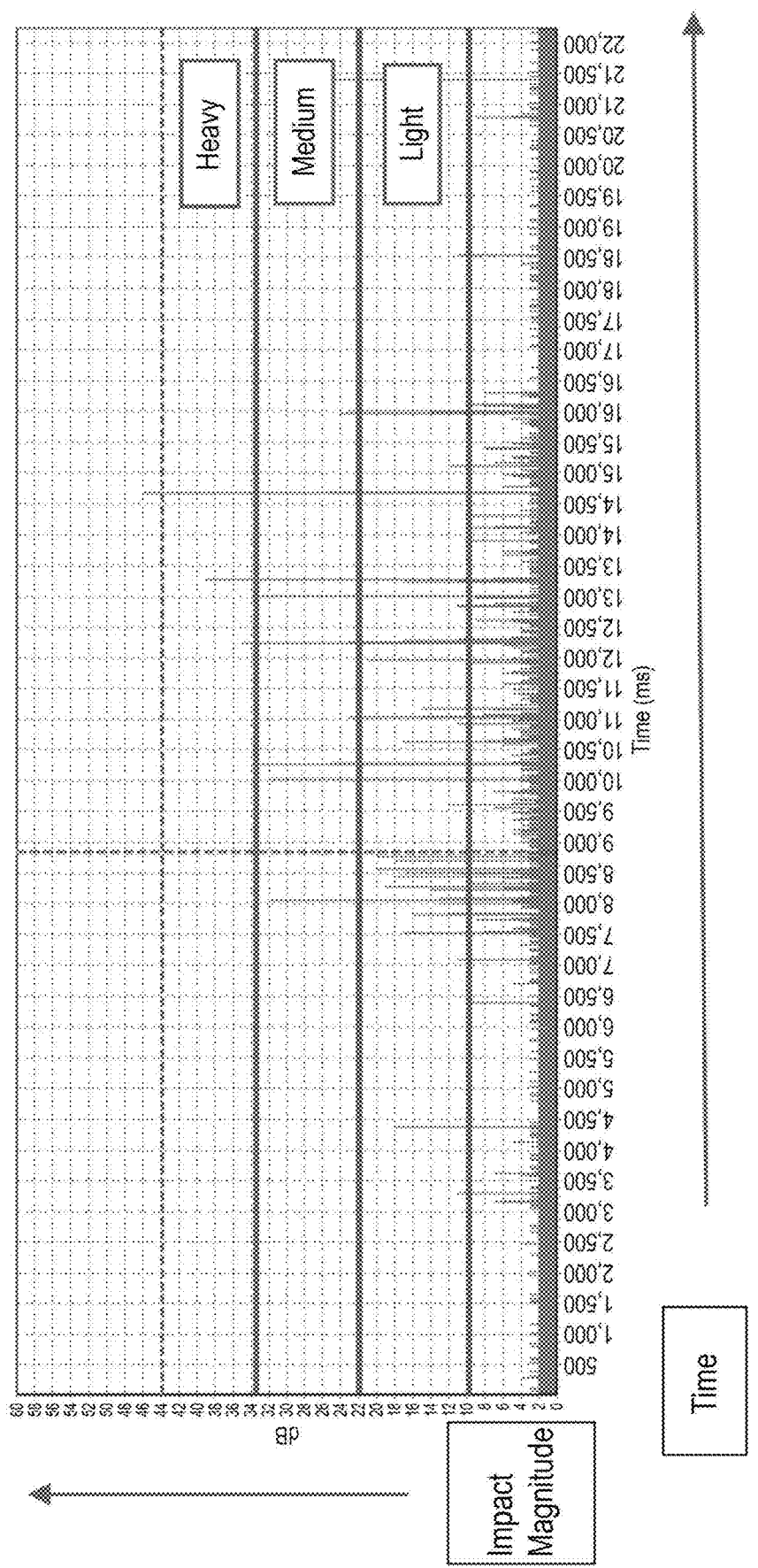
FIG. 7 shows the sensor system output for a fuel oil sample indicating heavy, medium, and light impacts.
Figure 8:
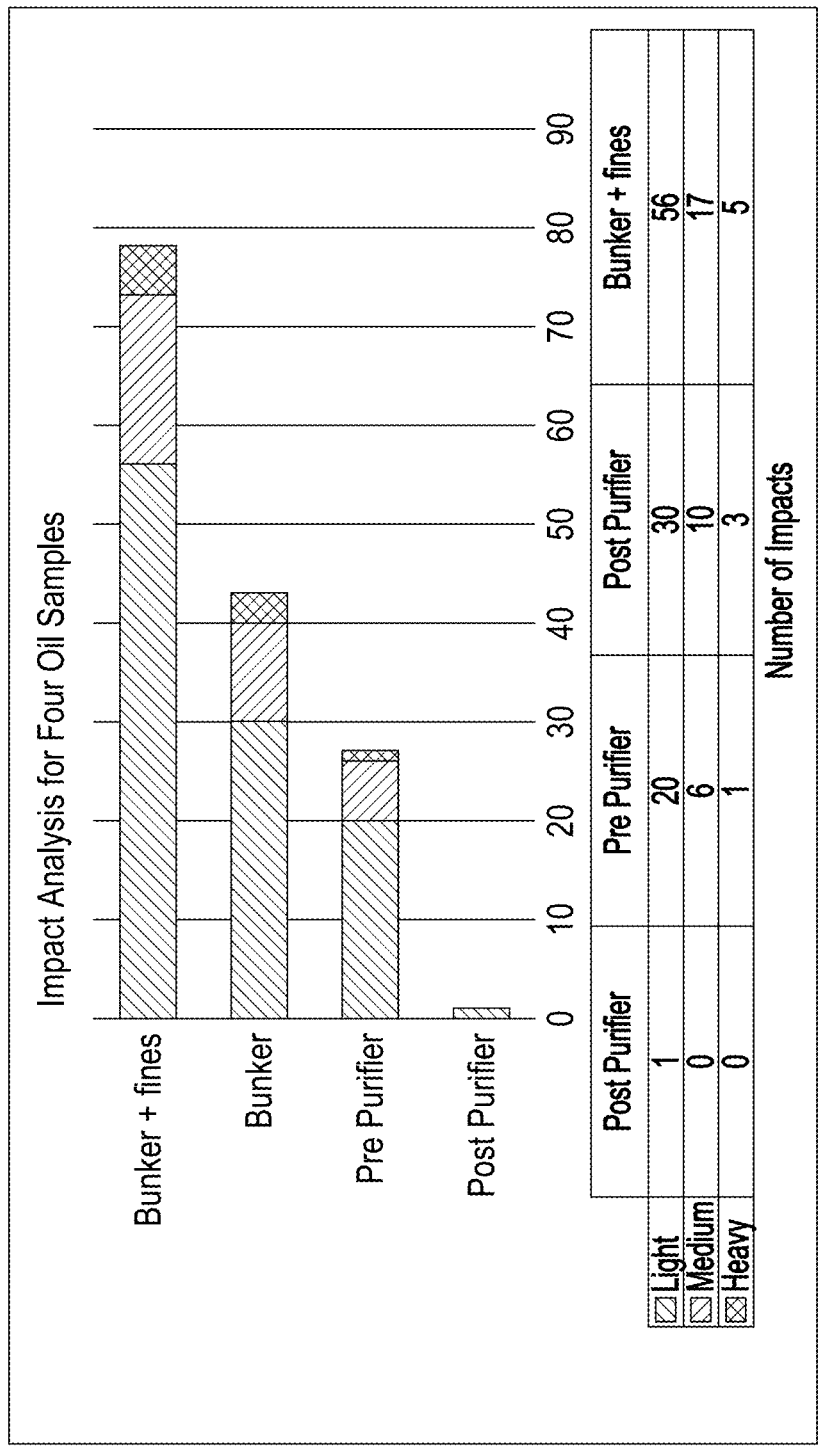
FIG. 8 shows an impact analysis for four oil samples: a bunker sample+fines (as per FIG. 6); a bunker sample; a pre-purifier sample (as per FIG. 4); and a post-purifier sample (as per FIG. 5).

FIG. 7 shows the sensor system output for a fuel oil sample indicating heavy, medium, and light impacts while FIG. 8 shows an impact analysis for four oil samples: a bunker sample+fines (as per FIG. 6); a bunker sample; a pre-purifier sample (as per FIG. 4); and a post-purifier sample (as per FIG. 5).

While this invention has been described in relation to certain embodiments it will be appreciated that various alternative embodiments can be provided without departing from the scope of the invention which is defined by the appending claims. For example, the methodology can be used for other particle containing fluid systems and the specific configuration of impactor, gauge body, and acoustic sensor can be varied while still conforming to the basic principles of the invention as claimed.

What is claimed is:

1. A sensor system for detecting particles within a fluid, the sensor system comprising:
i. a gauge body having a working surface for receiving a particle containing fluid;
ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
iii. a sensor configured to detect the signal generated by the particles impacting the impactor and provide an output signal.

2. A sensor system for detecting particles within a fluid, the sensor system comprising:
i. a gauge body having a working surface for receiving a particle containing fluid;
ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
iii. a sensor configured to detect the signal generated by the particles impacting the impactor and provide an output signal,
wherein the impactor is configured to be movable across the working surface of the gauge body whereby particles disposed over the working surface are impacted by the impactor to generate the signal.

3. The sensor system according to claim 2, wherein the sensor is further configured to detect elastic waves generated by particles impacting the impactor.

4. The sensor system according to claim 2, wherein the sensor is at least one of an acoustic emission sensor, an accelerometer, or an ultrasonic sensor.

5. The sensor system according to claim 2, wherein the sensor is mounted on, or embedded within, the gauge body.

6. The sensor system according to claim 2, wherein the sensor is mounted on, or embedded within, the impactor.

7. The sensor system as in claim 2, wherein the sensor is calibrated to provide an output signal which indicates one or both of particle size and particle concentration.

8. The sensor system according to claim 2, wherein the gauge body has more than one channel.

9. The sensor system according to claim 2, wherein the gauge body has one or more channels having a depth of not more than 100 micrometers, not more than 50 micrometers, not more than 25 micrometers, not more than 15 micrometers, or not more than 10 micrometers.

10. The sensor system according to claim 2, wherein the sensor system is configured such that the particle containing fluid is forcibly flowed through the spacing between the impactor and the working surface of the gauge body to cause particles to be impacted by the impactor thereby generating the signal.

11. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal, wherein the impactor is configured to be movable across the working surface of the gauge body in such a manner that the spacing between the impactor and the working surface decreases on moving the impactor across the working surface.

12. The sensor system according to claim 11, wherein the working surface of the gauge body is sloped or stepped such that the spacing between the impactor and the working surface decreases on moving the impactor across the working surface.

13. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal, wherein the gauge body comprises a channel, the channel having a first end, a second end, and a base forming the working surface for receiving the particle containing fluid, the impactor being configured to be movable along the channel in a direction from the first end to the second end whereby particles within the channel are impacted by the impactor generating the signal.

14. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal, wherein the impactor is supported over the working surface of the gauge body by a guide rail which is sloped relative to the working surface such that the spacing between the impactor and the base decreases on moving the impactor across the working surface.

15. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal, wherein the impactor is in the form of a slider which slides over the working surface of the gauge body.

16. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and
  iii. a sensor configured to detect the signal generated by the particles impacting the impactor and provide an output signal, wherein the impactor is in the form of a roller which rolls over the working surface of the gauge body.

17. A sensor system for detecting particles within a fluid, the sensor system comprising:
  i. a gauge body having a working surface for receiving a particle containing fluid;
  ii. an impactor spaced apart from the working surface of the gauge body defining a spacing between the impactor and the working surface of the gauge body through which particle containing fluid can pass, wherein the sensor system is configured such that as the particle containing fluid passes through the spacing between the impactor and the working surface of the gauge body, particles disposed over the working surface are impacted by the impactor generating a signal which is dependent on one or both of the size and concentration of particles in the fluid; and iii. a sensor configured to detect the signal generated by the particles impacting the impactor and provide an output signal, wherein the sensor system is configured such that the particle containing fluid is forcibly flowed through the spacing between the impactor and the working surface of the gauge body to cause particles to be impacted by the impactor thereby generating the signal, and wherein the spacing is in the form of an aperture which can be varied in size in order to detect particles of differing size.

18. A method of sensing particles in a particle containing fluid, the method comprising:
   i. loading a particle containing fluid onto a working surface of a gauge body;
   ii. providing an impactor spaced apart from the working surface of the gauge body defining a spacing between the impactor and the working surface of the gauge body through which particle containing fluid can pass, wherein as the particle containing fluid passes through the spacing between the impactor and the working surface of the gauge body, particles disposed over the working surface are impacted by the impactor generating a signal which is dependent on one or both of the size and concentration of particles in the fluid; and
   iii. detecting the signal generated by the particles impacting the impactor and providing an output signal.

19. The method according to claim 18, wherein the particle containing fluid is fuel oil containing catalytic fines.

20. The method according to claim 18, utilizing the sensor system according to claim 2.

21. The method according to claim 18, further comprising the step of moving the impactor across the working surface of the gauge body, whereby particles disposed over the working surface are impacted by the impactor to generate the signal.

* * * * *